United States Patent [19]

Groenke

[11] Patent Number: 5,573,004
[45] Date of Patent: Nov. 12, 1996

[54] ELECTRICALLY STABLE ELECTRODE AND SENSOR APPARATUS

[75] Inventor: Allen W. Groenke, Bloomington, Minn.

[73] Assignee: EdenTec Corporation, Eden Prairie, Minn.

[21] Appl. No.: 319,238

[22] Filed: Oct. 6, 1994

[51] Int. Cl.⁶ ....................................................... A61B 5/087
[52] U.S. Cl. ........................... 128/724; 128/736; 338/22 R
[58] Field of Search ..................................... 128/724, 721, 128/736; 338/22 R, 308

[56] References Cited

U.S. PATENT DOCUMENTS

| | | | |
|---|---|---|---|
| 3,232,288 | 2/1966 | Krobath | 128/2.08 |
| 3,241,549 | 3/1966 | Tyler | 128/2 |
| 3,766,908 | 10/1973 | Haynes | 128/2 |
| 3,884,219 | 5/1975 | Richardson et al. | 128/2 |
| 3,903,876 | 9/1975 | Harris | 128/2.08 |
| 3,906,936 | 9/1975 | Habal | 128/2 |
| 3,916,877 | 11/1975 | Beckman | 128/2.05 |
| 3,962,917 | 6/1976 | Terada | 73/204 |
| 3,999,537 | 12/1976 | Noiles | 128/2 |
| 4,036,211 | 7/1977 | Veth et al. | 128/2 |
| 4,146,957 | 4/1979 | Toenshoff | 29/612 |
| 4,176,660 | 12/1979 | Mylrea et al. | 128/671 |
| 4,183,136 | 1/1980 | Colla | 29/620 |
| 4,289,142 | 9/1981 | Kearns | 128/716 |
| 4,306,567 | 12/1981 | Krasner | 128/671 |
| 4,326,404 | 4/1982 | Mehta | 73/29 |
| 4,350,166 | 9/1982 | Mobarry | 128/664 |
| 4,366,821 | 1/1983 | Wittmaier et al. | 128/724 |
| 4,536,274 | 8/1985 | Papadakis et al. | 204/433 |
| 4,555,414 | 11/1985 | Hoover et al. | 427/43.1 |
| 4,567,888 | 2/1986 | Robert et al. | 128/204.21 |
| 4,595,016 | 6/1986 | Fertig et al. | 128/719 |
| 4,602,644 | 7/1986 | DiBenedetto et al. | 128/725 |
| 4,745,925 | 5/1988 | Dietz | 128/725 |
| 4,756,756 | 7/1988 | Cassat | 106/20 |
| 4,777,963 | 10/1988 | McKenna | 128/724 |
| 4,818,827 | 4/1989 | Ipcinski et al. | 200/5 |
| 4,878,502 | 11/1989 | Dietz | 128/725 |
| 4,923,401 | 5/1990 | Marshall et al. | 434/22 |
| 4,971,065 | 11/1990 | Pearce | 128/721 |
| 5,036,859 | 8/1991 | Brown | 128/734 |
| 5,081,866 | 1/1992 | Ochiai et al. | 73/204.21 |
| 5,100,695 | 3/1992 | Kawakami et al. | 427/96 |
| 5,190,048 | 3/1993 | Wilkinson | 128/724 |
| 5,265,624 | 11/1993 | Bowman | 128/848 |
| 5,311,875 | 5/1994 | Stasz | 128/724 |
| 5,394,883 | 3/1995 | Neuman | 128/724 |

Primary Examiner—Lee S. Cohen
Attorney, Agent, or Firm—Nawrocki, Rooney & Sivertson

[57] ABSTRACT

An apparatus and method for electrically stable electrodes and sensors having a flexible base or substrate. One or more flexible and pressure sensitive resistors having a high resistance and a high temperature coefficient of resistivity are printed on a first surface of the flexible base, and a second set of one or more substantially identical resistors are printed on a second surface such that each resistor on the second surface is directly opposite a resistor on the first surface. The opposing resistors are then electrically interconnected in mating pairs, so that when the substrate is flexed, one resistor of each pair is compressed and the other is tensed with the result that the changes in resistance cancel one another.

18 Claims, 5 Drawing Sheets

ELECTRICALLY STABLE ELECTRODE AND SENSOR APPARATUS

BACKGROUND OF THE INVENTION

1. Field of the Invention

The present invention generally relates to electrodes for sensing or stimulating or both, and more particularly the present invention relates to electrodes and sensors carried on a flexible substrate. Still more particularly the present invention relates to respiration sensor technology for detecting abnormal breathing of a client.

2. Description of the Prior Art

It is known in the prior art to employ respiration sensors to monitor patients' susceptible to sleep apnea and other disorders of the respiration system. U.S. Pat. No. 4,878,502 discusses a breathing sensor employing a tubular passage in which a ball is free to move to break a beam of light. The ball is moved in response to the flow of air associated with the breathing of a patient. An optoelectric inhalation sensor using thin film deposition is disclosed in U.S. Pat. No. 4,745,925.

Acoustic sensors for monitoring respiration are mentioned in U.S. Pat. Nos. 4,602,664 and 4,595,016. U.S. Pat. No. 4,366,821 shows a respiration monitoring system that preferably uses a gas sensor, and U.S. Pat. No. 4,350,166 discloses the use of a video monitor. U.S. Pat. No. 4,326,404 discloses the use of a sodium chloride crystal to sense moisture.

A pressure sensor for respiration monitoring is taught in U.S. Pat. No. 4,306,867. U.S. Pat. No. 4,289,142 teaches the use of an impedance plethysmograph for respiration sensing. The use of thermoresistive sensors for monitoring is suggested in U.S. Pat. Nos. 3,903,876; 3,884,219; and 3,999,537.

The advantages of providing multiple sensors on a single flexible substrate are taught in U.S. patent application Ser. No. 08/182,424, filed Jan. 18, 1994 by Bowman et al. This Bowman et al Application discusses employing a plurality of sensor electrodes positioned at the various orifices which vent the upper airway of a patient; normally the two nostrils and the mouth.

A continuing disadvantage with this and other prior art which employs flexible substrates is that when the substrate is flexed, the resulting pressure on the sensor electrodes causes changes in their electrical and thermoresistive specifications.

SUMMARY OF THE INVENTION

The present invention overcomes the disadvantages found in the prior art by providing, for each sensor electrode mounted on the sensing surface of the substrate, at least one further essentially similar electrode mounted on the opposite side of the substrate and electrically connected to its related sensing electrode. As the substrate is flexed the result is to bend the sensor and its similar electrode in opposite directions such that the resistive change in the electrode under compression is counteracted by the resistive change in the electrode under tension.

Another advantage of the present invention is found when the cause of the change is the breath of a patient impinging on the thermoresistive sensing electrode. The related electrode will receive the residual heat caused by the airflow to the opposite side of the substrate and thus the overall change in resistance will be increased due to the electrodes on both sides of the substrate being electrically connected, for example, in series.

Though the advantages of connecting an electrode on one side of a flexible substrate with a substantially identical mate electrode on the opposite side of the substrate have been described above with reference to the improved respiration sensor of this invention, it will be apparent to one of skill in the art that there are other valuable uses for this unique combination of elements and the method of manufacturing them. For example, the above described combination of electrodes could be used for stimulating portions of a patient's body, and the correction of electrical pressure changes would advantageously effect the stimulation by keeping the overall resistance of the stimulating electrode more stable.

BRIEF DESCRIPTION OF THE DRAWINGS

These and other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 3 is a perspective sectional view taken along section line 3—3 of FIG. 2a;

DETAILED DESCRIPTION OF THE PREFERRED EMBODIMENTS

Figure 1:
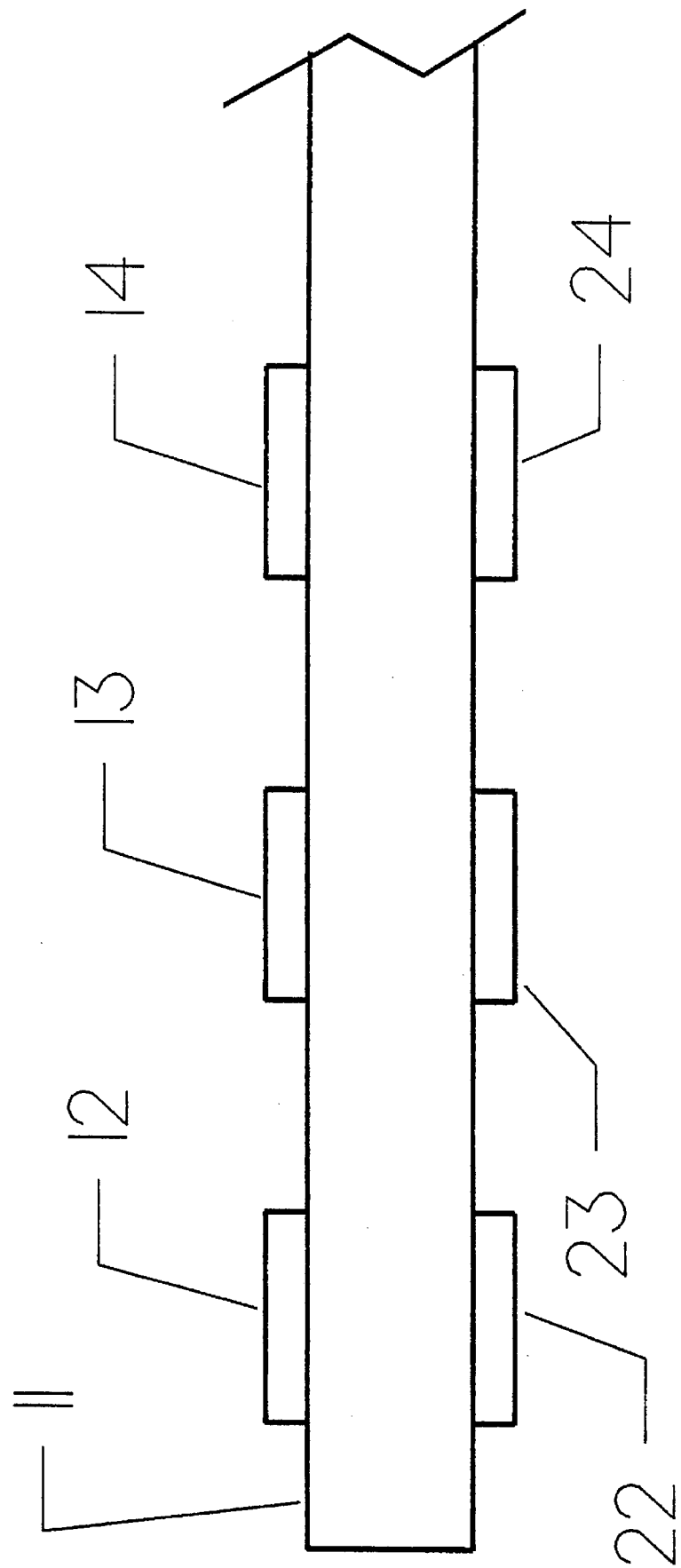
FIG. 1 is an exemplary plan view showing a portion of a flexible substrate with mated pairs of essentially similar electrodes mounted on opposite sides of the substrate.
Figure 2A:
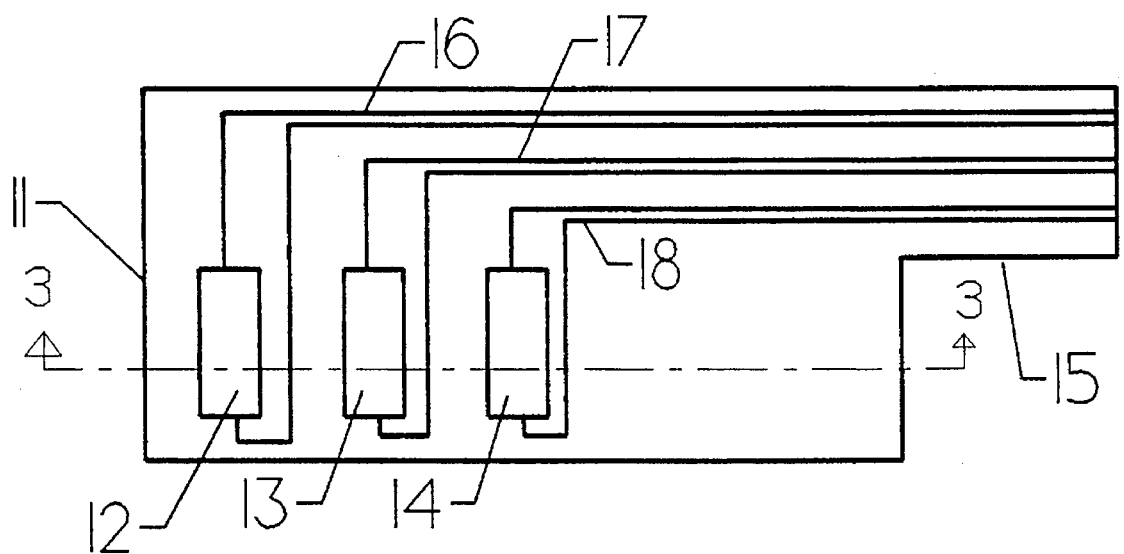
FIG. 2a is an plan view of the upper surface of the substrate of FIG. 1.
Figure 2B:
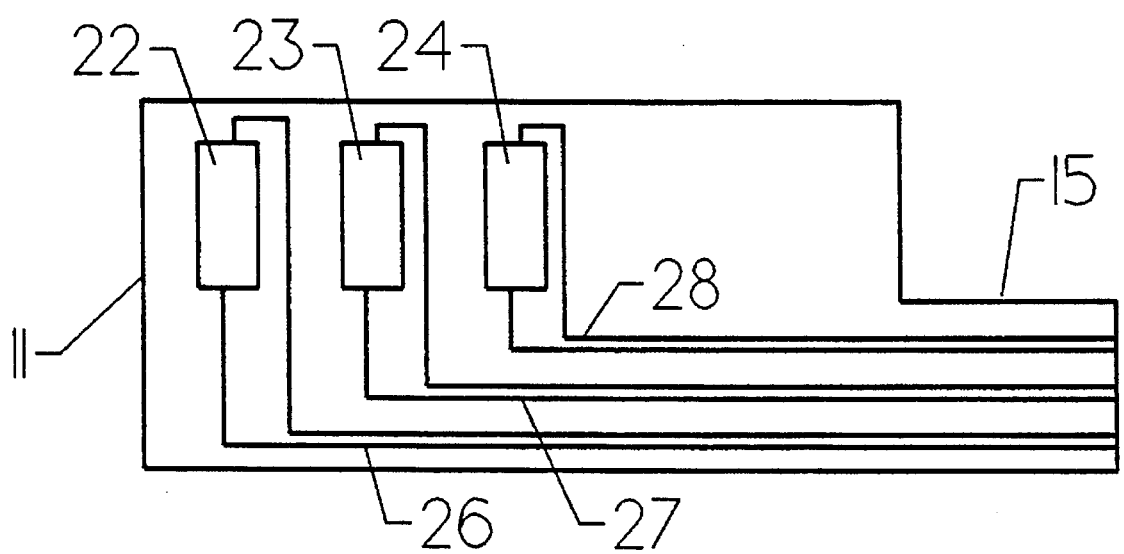
FIG. 2b is a plan view of the lower surface of the substrate of FIG. 1.
Figure 3:
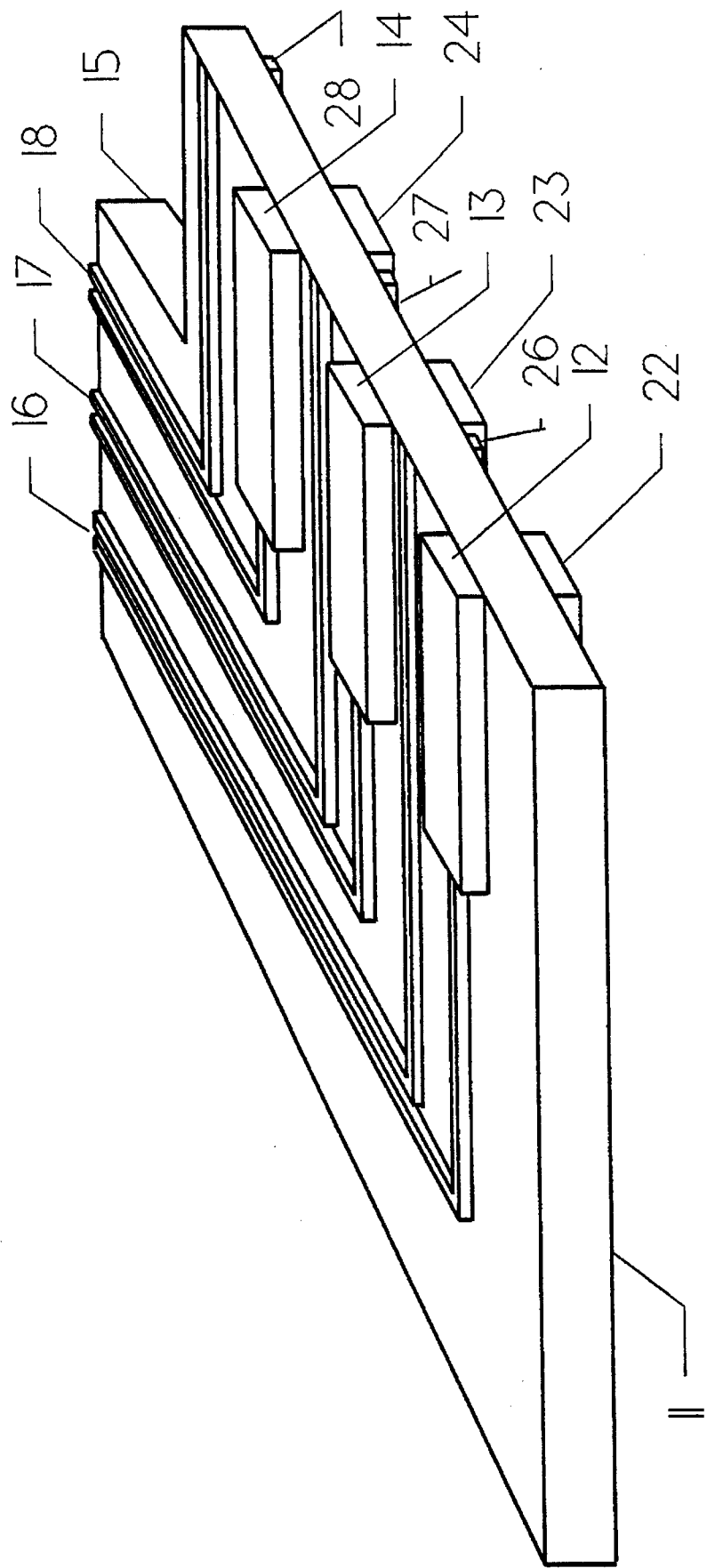
Figure 4:
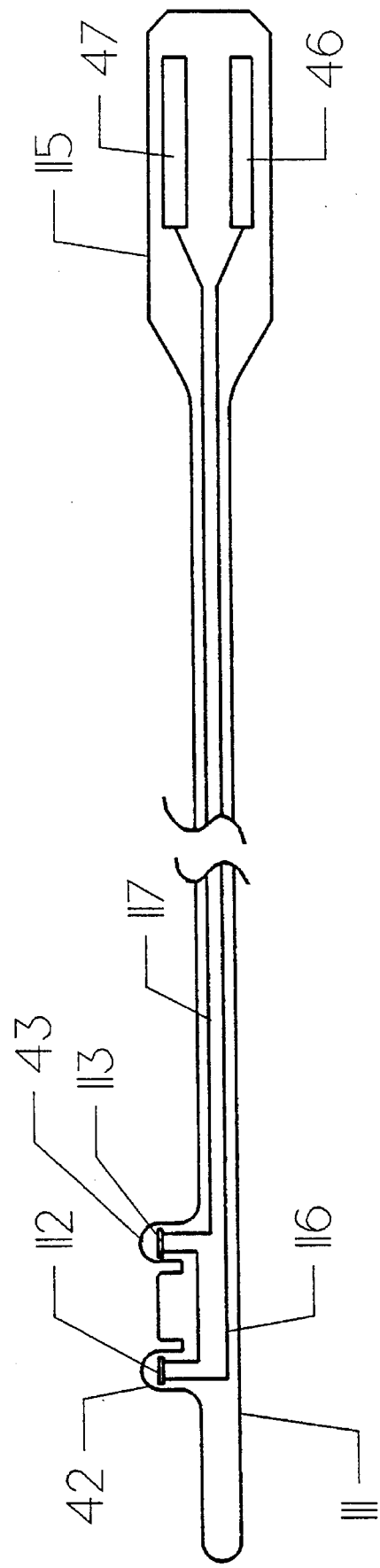
FIG. 4 is a partial plan view of a first surface of a flexible substrate in a respiration sensor utilizing the apparatus of this invention.
Figure 5:
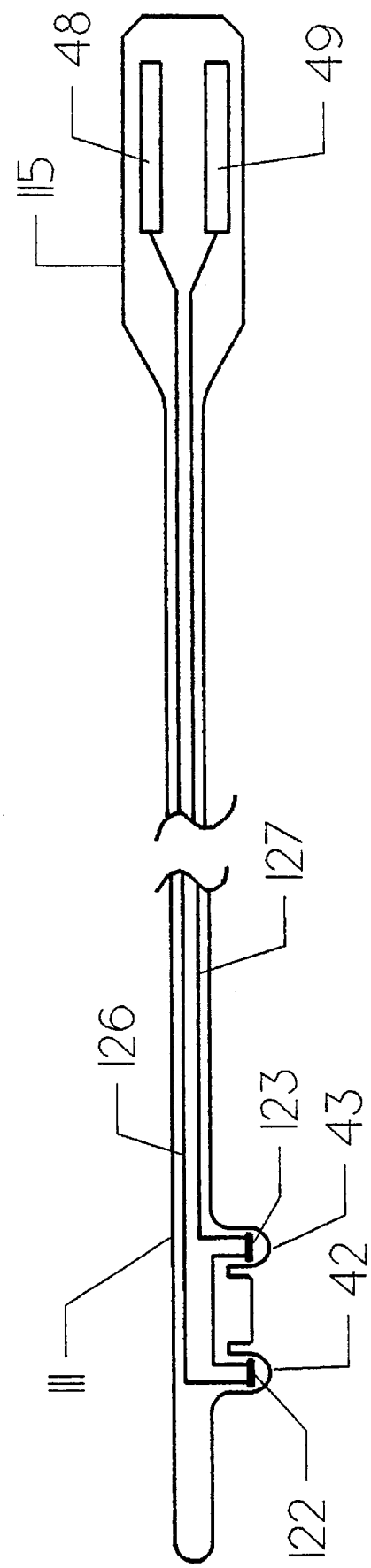
FIG. 5 is a partial plan view of a second surface of the respiration sensor of FIG. 4.

As will be apparent from the following discussion, FIGS. 1–3 are intended to be exemplary or representative of the general apparatus of this invention. FIGS. 4 and 5 disclose a preferred embodiment of this invention as used in a respiration or airflow sensor.

FIG. 1 shows a portion of a flexible substrate 11. Mounted on a first side of substrate 11 are a plurality of resistor elements 12, 13 and 14. Mounted on the opposite side of substrate 11 are another plurality of substantially identical resistor elements 22, 23 and 24. It is important to note that though this preferred embodiment of the apparatus of this invention uses a plurality of pairs or mates of resistors the invention will be effective even with one pair of resistor elements.

FIG. 2a shows a top or upper side view of substrate 11, which is here shown as having a connector tab 15 adapted to be joined to an electrical connector (not shown). Resistor elements 12, 13 and 14 are electrically connected to tab 15 through, respectively, electrical path pairs 16, 17 and 18.

FIG. 2b shows a bottom or lower side view of substrate 11 and connector tab 15. Resistor elements 22, 23 and 24 are electrically connected to tab 15 through, respectively, electrical path pairs 26, 27 and 28. It is apparent that the bottom view of substrate 11 as shown in FIG. 2b is essentially a mirror image of the top view of substrate 11 shown in FIG. 2a. Each mated pair of resistors, 12 and 22, 13 and 23, and 14 and 24 preferably comprise substantially identical resistors. In the preferred embodiment, all of the resistor elements have a resistance value that fluctuates or changes with pressure variations, and each of the resistor elements may be thermoresistive such that its electrical value may also change with temperature variations. Further, in the preferred embodiment the joinder of connector tab 15 to a connector (not shown) results in the electrical connection of each of resistors 12, 13 and 14 in parallel with its mated resistor, 22, 23 or 24.

FIG. 3 shows a perspective sectional view of substrate 11 with connector tab 15, the section taken along section line 3—3 of FIG. 2a. It again becomes apparent how mated pairs of resistors 12 and 22, 13 and 23, and 14 and 24 are mounted on opposing sides of substrate 11. Also shown are electrical path pairs 16, 17 and 18 connecting resistors 12, 13 and 14, respectively, to tab 15. (Electrical path pairs 26, 27 and 28 are present but only partially visible in FIG. 3 for the purpose of connecting, respectively, resistors 22, 23 and 24 to tab 15, as is clearly shown in FIG. 2b.)

From FIGS. 1–3 it is apparent that as substrate or base 11 is flexed each mated pair of resistors will flex in opposite directions to one another. For example, if resistor 12 is placed under compression, its paired resistor 22 will be placed under tension. As a result, because the pair of resistors are connected in parallel, the opposite changes in resistance values of the two resistor elements should be essentially off-setting. Thus the apparatus and the method of connection of this invention creates a substantially stable electrical resistance on the flexible substrate to reduce or remove disadvantages of the prior art caused by unavoidable resistance changes due to flexing of the base or substrate holding the resisters. This advantage prevails no matter what the device may be which utilizes the invention, as long as the device requires a flexible base on which are mounted one or more resistance elements that will flex when the base flexes.

Another use for the apparatus and method of FIGS. 1–3 is as a temperature sensor. For example, if resistors 12, 13 and 14 are of a thermoresistive material, such as carbon, and are situated directly in an air flow path, such as under the nostrils of a patient, the flow of air impinging on the resistors will cause a temperature change and thus alter the resistance value of each resistor. With the addition of the substantially similar mating resistors, 22, 23 and 24, a certain amount of residual air flow will reach around substrate 11 to impinge upon and change the resistance value of these added resistors as well. Because each of elements 22, 23 and 24 is connected to its respective mate 12, 13 or 14 through connector tab 15, the additional sensing of the air flow will increase the reliability and sensitivity of the sensing device.

It will be apparent that though using a plurality of resistors on each side of the flexible base has been described as preferred, the use of a single resistor with one mate will also fall within the scope of this invention and offer similar advantages over the prior art.

For the preferred embodiments of FIGS. 1–3 described above, flexible base or substrate 11 may be any one of a plurality of such apparatus well known and widely used in the art. Resistor or sensing elements 12–14 and 22–24 may be produced using several known technologies. In the preferred embodiments, a conductive ink having a high temperature coefficient of resistance and high resistance may be applied to a first side of base 11 using a silk screening process; thus producing resistor elements 12–14. Mating elements on the other side of base 11 may be produced in a similar manner to create mating resistor elements 22–24. Conductive paths 16–18 and 26–28 may preferably comprise a conductive ink having a low resistance and a low temperature coefficient of resistance. Normally the interconnecting electrical paths are silk screened on their respective side of base or substrate 11 in a separate step from the printing of the resistance or sensing elements.

Though each mated pair of resistors is preferably connected in parallel, it is apparent that each mated pair of resistors could be connected in series and still offer the same advantages over the prior art. Further, each of the parallel-connected mated pairs on either side of the substrate are preferably connected in series with one another, though it is apparent that they could as well be connected in parallel without departing from the scope and advantages of the present invention.

Referring now to FIG. 4, there is shown a partial plan view of a respiratory air flow sensor utilizing the apparatus and method of this invention. A first surface of a substrate 111 is shown having a pair of projections 42 and 43 on which are printed a set of carbon bars 112 and 113, respectively. Conductive ink bars 112 and 113 are carbon-based to give them a relatively high resistance and a relatively high temperature coefficient of resistance.

A connector tab 115 is shown having a set of connector bars 46 and 47 mounted thereon, and a silver conductive ink is printed on substrate 11 to print electrical conductive paths 116 and 117 that connect bars 112 and 113 in series to tab 115 and connector bars 46 and 47.

FIG. 5 shows the opposite surface of substrate 111 and projections 42 and 43 on which are printed another set of carbon-based conductive ink bars 122 and 123 that are substantially identical to bars 112 and 113 of FIG. 4. A set of connector bars 48 and 49 are printed on the opposite side of connector tab 115, and silver conductive ink is again used to print electrical conductive paths 126 and 127 that connect bars 122 and 123 in series to tab 115 and connector bars 46 and 47.

When tab 115 is joined to its connector (not shown), the electrical path including bars 112 and 113 is mated in parallel with the electrical path including bars 122 and 123. The mated paths may be connected in series rather than parallel if desired. Power is also applied at the time of connection of tab 115 to its connector.

When the sensor of FIGS. 4 and 5 is applied to a patient projections 42 and 43 are situated under the nostrils such that warm air is expelled directly onto carbon bars 112 and 113 on the patient side of base 111 to warm bars 112 and 113 and cause a change in their resistance. Bars 122 and 123 on the opposite side of base 111 will be exposed to the warmth of residual amounts of expired air and will also have a change in resistance. Because of the electrical connection between mating pairs of bars 112 and 123, as well as 113 and 123, the warm air flow from the patient's nostrils will be sensed with a greater sensitivity and more reliability than in prior art devices.

Further, as more fully described above in the discussion of FIGS. 1–3, when projections 42 and 43 are flexed, the resultant resistance drop in the bar under compression will be counteracted by the mating bar under tension, thus making the overall resistance change essentially zero. Having thus described the preferred embodiments of the present invention, those of skill in the art will readily appreciate the other useful embodiments within the scope of the attached claims.

I claim:

1. In a sensor apparatus including an insulative substrate having a first side, and a first thermal responsive impedance path attached to the first side of the substrate, the improvement comprising:

a. a second side of the substrate opposite to the first side;

b. a second thermal responsive impedance path attached to said second side of the substrate; and c. electrical conductive path means on the first and second sides of the substrate for electrically connecting said first and second impedance paths.

2. The apparatus of claim 1 in which:

the substrate and said first and second impedance paths are flexible; and said first and second impedance paths are pressure responsive.

3. The apparatus of claim 1 or 2 in which:

said first and second impedance paths are substantially identical.

4. The apparatus of claim 1 or 2 in which:

said first and second impedance paths are connected in series.

5. The apparatus of claim 1 or 2 in which:

said first and second impedance paths are connected in parallel.

6. The apparatus of claim 1 or 2 in which:

said second impedance path is mounted on said second side of the substrate directly opposite said first impedance path.

7. The apparatus of claim 1 or 2 in which:

each of said first and second impedance paths comprises a plurality of impedance paths.

8. The apparatus of claim 3 in which:

said first and second impedance paths are connected in series.

9. The apparatus of claim 3 in which:

said first and second impedance paths are connected in parallel.

10. The apparatus of claim 3 in which:

said second impedance path is mounted on said second side of the substrate directly opposite said first impedance path.

11. The apparatus of claim 3 in which:

each of said first and second impedance paths comprises a plurality of impedance paths.

12. In a respiration sensor having a flexible substrate, a plurality of sensing resistors printed on a first surface of said substrate, each of said sensing resistors being pressure and temperature variable, and a plurality of first conductive paths printed on said substrate connected to said sensing resistors and a connector, the improvement comprising:

a. a plurality of mating resistors printed on a second surface of said substrate opposite to said first surface;

b. each of said mating resistors being printed directly opposite one of said sensing resistors to form a sensing pair;

c. a plurality of second conductive paths printed on said second surface of said substrate connected to said mating resistors; and connection means for electrically interconnecting each sensing pair of resistors.

13. The respiration sensor of claim 12 in which:

the sensing and mating resistors comprise a first conductive ink having a high resistance and a high temperature coefficient of resistivity.

14. The respiration sensor of claims 12 or 13 in which:

said conductive paths comprise a second conductive ink having a low resistance and a low temperature coefficient of resistivity.

15. The respiration sensor of claims 12 or 13 in which each of said sensing pairs comprise:

a sensing resistor and a mating resistor electrically connected in parallel.

16. The respiration sensor of claims 12 or 13 in which each of said sensing pairs comprise:

a sensing resistor and a mating resistor electrically connected in series.

17. The respiration sensor of claim 15 in which each of said sensing pairs comprise:

a sensing resistor and a mating resistor electrically connected in parallel.

18. The respiration sensor of claim 14 in which each of said sensing pairs comprise:

a sensing resistor and a mating resistor electrically connected in series.

* * * * *